(12) United States Patent
Ohga et al.

(10) Patent No.: US 9,211,543 B2
(45) Date of Patent: Dec. 15, 2015

(54) HOLDER FOR TRANSFERRING TEST TUBE

(71) Applicant: HITACHI HIGH-TECHNOLOGIES CORPORATION, Tokyo (JP)

(72) Inventors: Hiroshi Ohga, Tokyo (JP); Tatsuya Fukugaki, Tokyo (JP); Tetsuya Isobe, Tokyo (JP); Kuniaki Onizawa, Tokyo (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/355,083

(22) PCT Filed: Dec. 14, 2012

(86) PCT No.: PCT/JP2012/082442
§ 371 (c)(1),
(2) Date: Apr. 29, 2014

(87) PCT Pub. No.: WO2013/099647
PCT Pub. Date: Jul. 4, 2013

(65) Prior Publication Data
US 2014/0301916 A1    Oct. 9, 2014

(30) Foreign Application Priority Data

Dec. 28, 2011   (JP) ................................ 2011-287249

(51) Int. Cl.
*B01L 9/06*    (2006.01)
*G01N 35/04*   (2006.01)
*G01N 35/00*   (2006.01)

(52) U.S. Cl.
CPC . *B01L 9/06* (2013.01); *G01N 35/04* (2013.01); *B01L 2200/025* (2013.01); *B01L 2300/022* (2013.01); *B01L 2300/12* (2013.01); *G01N 2035/00801* (2013.01)

(58) Field of Classification Search
CPC .......................... B01L 9/06; G01N 2035/00801
USPC .................................................. 422/561–562
See application file for complete search history.

(56) References Cited

U.S. PATENT DOCUMENTS

| | | | | |
|---|---|---|---|---|
| 4,383,422 A | * | 5/1983 | Gordon et al. | ............... 62/457.4 |
| 5,897,090 A | | 4/1999 | Smith et al. | |
| 5,941,366 A | * | 8/1999 | Quinlan et al. | ............ 198/465.1 |
| 6,971,506 B2 | | 12/2005 | Hassinen et al. | |

(Continued)

FOREIGN PATENT DOCUMENTS

| | | |
|---|---|---|
| EP | 2765426 A1 | 8/2014 |
| JP | 46-719 Y1 | 1/1971 |

(Continued)

OTHER PUBLICATIONS

Extended European Search Report received in corresponding European Application No. 12862553.0 dated Jul. 8, 2015.

*Primary Examiner* — Paul Hyun
(74) *Attorney, Agent, or Firm* — Mattingly & Malur, PC

(57) ABSTRACT

A test tube holder holds various types of test tubes substantially perpendicular, and is structured to be durable against extraction and insertion of the test tubes. The test tube holder includes a housing part having a hollow portion, a holding part positioned on an upper side of the housing part and having an opening portion, which accepts a test tube, and a housing portion, which houses the accepted test tube. An elastic part is formed inside the holding part so as to abut on the housed test tube. The test tube holder has a weight housed inside the hollow portion. The holding part and the elastic part may be integrally formed. Inside the hollow portion of the housing part, besides the weight, an individual identification tag, an electromagnetic wave absorbent, and a support member for a tapered test tube can be housed in accordance with usage.

20 Claims, 7 Drawing Sheets

(56) References Cited

U.S. PATENT DOCUMENTS

| | | |
|---|---|---|
| 2005/0207945 A1 | 9/2005 | Itoh |
| 2007/0181403 A1 | 8/2007 | Sheets et al. |
| 2010/0089803 A1 | 4/2010 | Lavi et al. |
| 2011/0182784 A1 | 7/2011 | Suzuki et al. |
| 2012/0174687 A1 | 7/2012 | Ohga et al. |

FOREIGN PATENT DOCUMENTS

| | | |
|---|---|---|
| JP | 59-9692 Y2 | 3/1984 |
| JP | 11-218537 A | 8/1999 |
| JP | 2005-262041 A | 9/2005 |
| JP | 2007-528329 A | 10/2007 |
| JP | 2010-78344 A | 4/2010 |
| JP | 2010-271204 A | 12/2010 |
| WO | 96/27442 A1 | 9/1996 |
| WO | 96/36437 A1 | 11/1996 |
| WO | 02/082095 A1 | 10/2002 |
| WO | 2010/042722 A1 | 4/2010 |
| WO | 2011/040203 A1 | 4/2011 |

* cited by examiner

FIG. 1
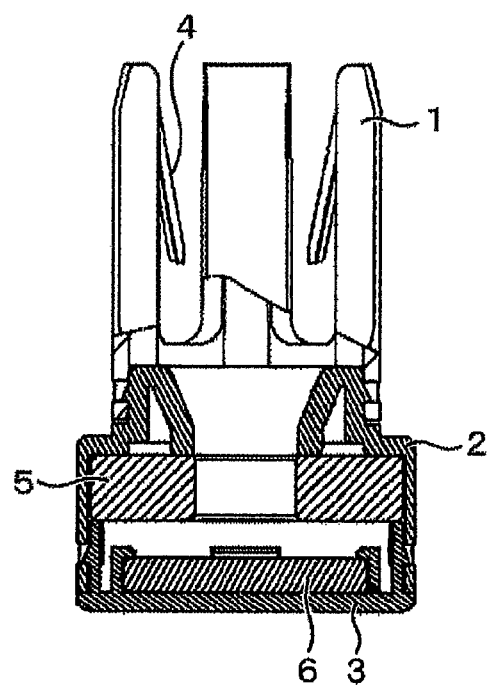
FIG. 2-A
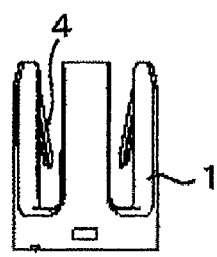
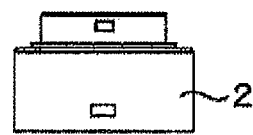
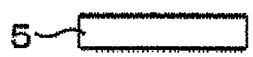
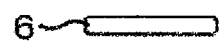
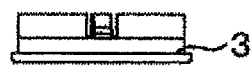

FIG. 2-B
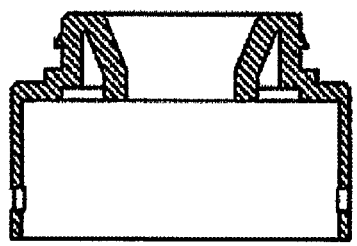
FIG. 2-C
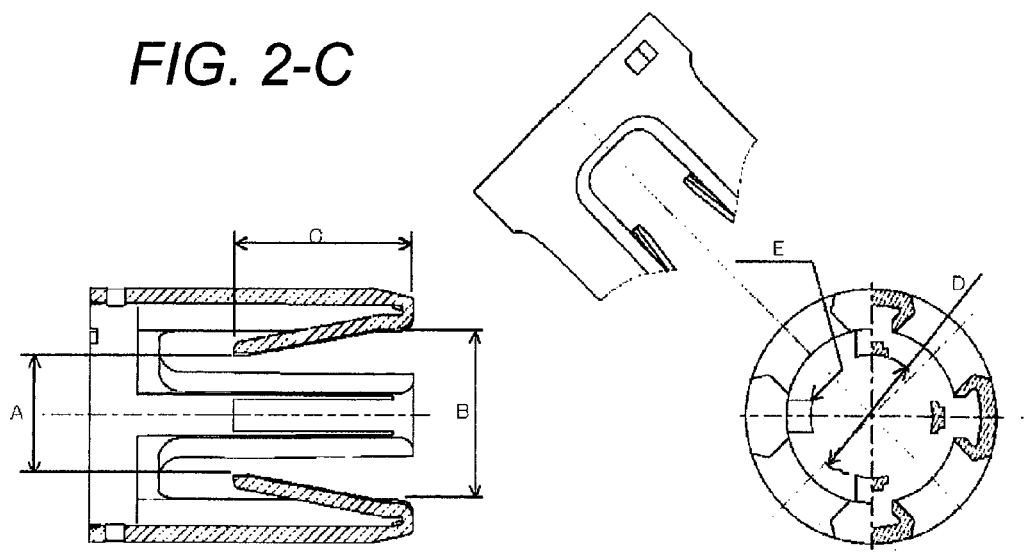
FIG. 3
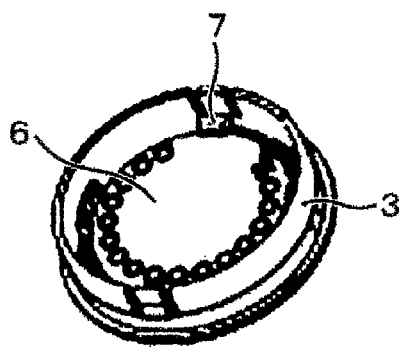

FIG. 10
(a)
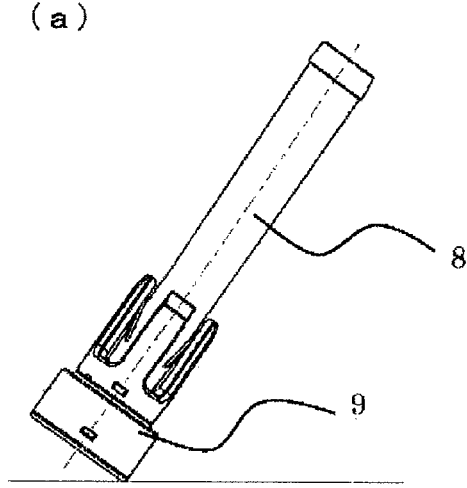
(b)
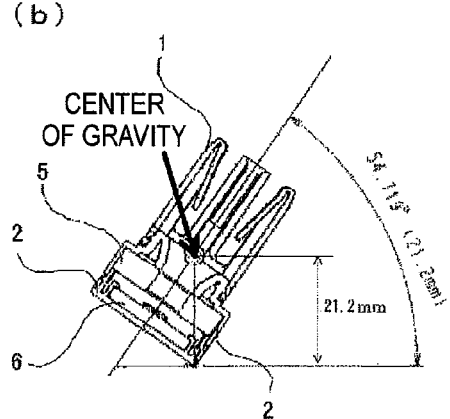
(c)
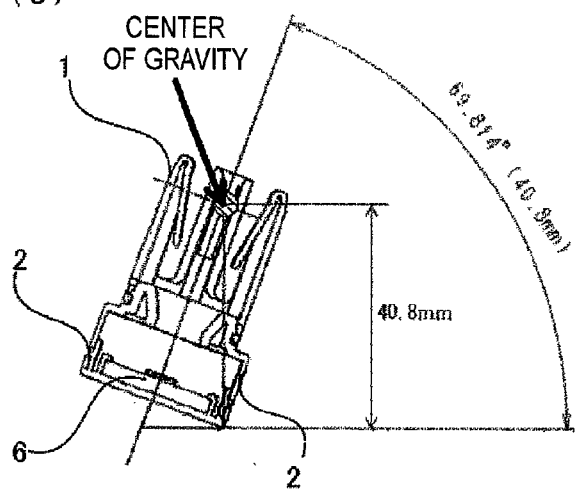

HOLDER FOR TRANSFERRING TEST TUBE

TECHNICAL FIELD

The present invention relates to an examiner holder used for transferring a test tube holding a specimen such as blood, urine, or a body fluid therein mainly on a belt conveyer to an automatic analysis apparatus.

BACKGROUND ART

At a large-scale hospital and an examination center, which analyze a large amount of specimen such as blood, automation of transferring and pre-processing the specimen is advancing for the purpose of improving examination efficiency and of decreasing contact between an operator and the specimen such as the blood. The specimen such as the blood is processed being housed in a container such as a test tube and a cup on which a label is attached. A barcode and the like are printed on the label.

As an outside diameter of the test tube, approximately $\phi 16$ or $\phi 13$ is most often used; however, there is variation of about several millimeters among manufacturers. Furthermore, some have a tapered external shape, whereby an outside diameter of a bottom of the container is shaped to be smaller than an outside diameter of an opening portion of the container.

These test tubes, while being placed on a test tube holder, are transferred by a transferring apparatus such as a transfer line to a pre-processing apparatus and an analysis apparatus. Patent Literature 1 discloses a general system using the test tube holder. In this system, the test tube is inserted into the test tube holder at a feeding part of the specimen, and processing such as extraction and insertion of the test tube is repeated at a storing part of the specimen and during intermediate processes. Furthermore, it is necessary for the test tube holder to hold the test tubes having different external shapes substantially perpendicular. Therefore, as in Patent Literatures 2, 3, and the like, in a holding structure, an elastic spring of metal or the like is installed facing upward in many cases.

CITATION LIST

Patent Literature

Patent Literature 1: WO 2011040203 A
Patent Literature 2: JP 2010-271204 A
Patent Literature 3: JP 2005-262041 A

SUMMARY OF INVENTION

Technical Problem

Since a test tube holder repeatedly undergoes processes such as insertion and extraction of a test tube many times within a system, a certain degree of durability is required for a spring portion, which is in general formed of an elastic body such a metal. Furthermore, the insertion of the test tube into the test tube holder is performed by an operator or a robot, and the test tube or a central axis of the test tube is not necessarily inserted perpendicular to a central axis of an insertion part where the test tube holder receives the test tube. Therefore, as described in the conventional technique, in a case where an adapter for holding the test tube or a holding part is formed to face upward, the adapter or the holding part may collide with the test tube, whereby a metallic spring of the test tube holder may be deformed after a long time of use.

Furthermore, the test tube holder disclosed in the conventional technique has a structure in which the metallic spring and a resin main body are combined, whereby there is a problem in that a cost reduction is difficult due to a high manufacturing cost and a large number of production man-hours as well as in that it is specialized in holding test tubes having a specific shape and is not suitable for holding many types of test tubes.

In view of the above-described problem, an objective of the present invention is to provide a test tube holder having high durability and with which the cost thereof can be reduced.

Solution to Problem

A structure of the present invention is as below. That is, a test tube holder is configured to include: a housing part having a hollow portion therein; a holding part positioned on an upper side of the housing part and having an opening portion, which accepts a test tube, and a housing portion, which houses the accepted test tube; and an elastic part formed inside the holding part so as to abut on the housed test tube. It has a weight housed inside the hollow portion.

Furthermore, the holding part having a storing portion for storing the test tube and the elastic part formed inside the holding part so as to abut on the stored test tube may be formed of the same material.

Furthermore, the housing, the holding part having the storing portion for storing the test tube, and the elastic part formed inside the holding part so as to abut on the stored test tube may be formed of the same material.

Advantageous Effects of Invention

According to the present invention, it is possible to provide a test tube holder having a good stability during transfer and that does not damage or contaminate the test tube or the holder itself even when the test tube is repeatedly put in and taken out.

Furthermore, as another effect of the present invention, it is possible to provide a test tube holder at a low manufacturing cost.

Furthermore, as still another effect of the present invention, it is possible to provide a test tube holder that can easily supply various types of test tube holders at a low cost in accordance with usage.

BRIEF DESCRIPTION OF DRAWINGS

FIG. 1 is a sectional view illustrating a test tube holder according to Embodiment 1 of the present invention.

FIG. 2-A is a view illustrating a configuration of the test tube holder according to Embodiment 1 of the present invention.

FIG. 2-B is a sectional view illustrating a main body housing.

FIG. 2-C is a detailed view illustrating a housing with a spring.

FIG. 3 is a view illustrating an example of assembling a housing with a lid-like bottom part and a radio wave individual identification tag.

FIGS. 10(a) to 10(c) are views illustrating a position of a center of gravity of a specimen holder.

DESCRIPTION OF EMBODIMENTS

Hereinafter, embodiments of the invention are described in detail with reference to the drawings.

[Embodiment 1]

Figure 4:
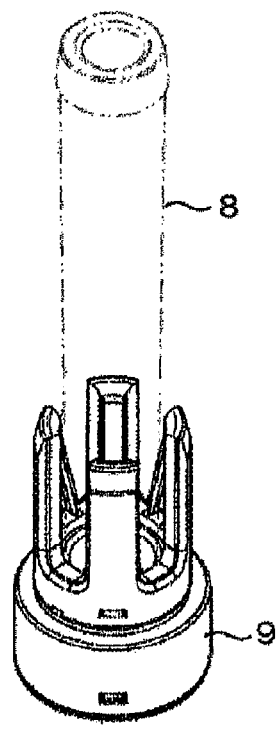
FIG. 4 is a view illustrating the test tube holder according to Embodiment 1 of the present invention.
Figure 5:
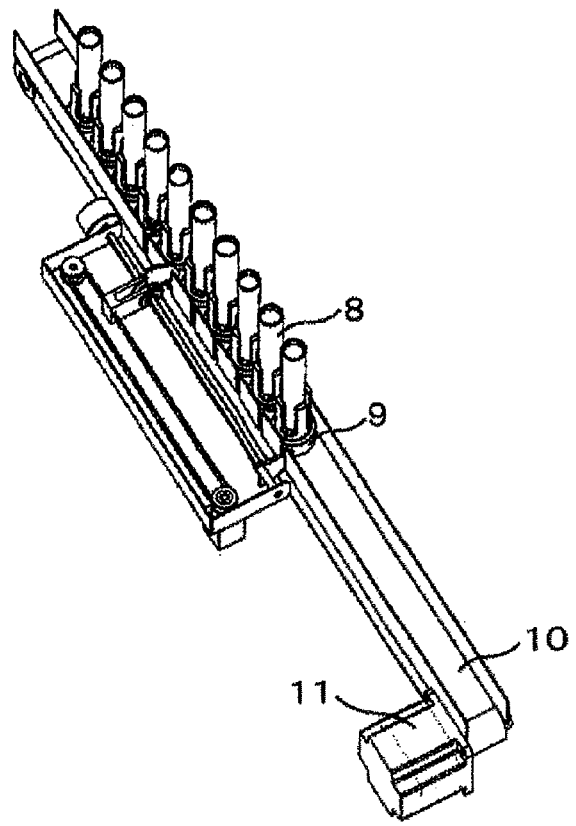
FIG. 5 is a view illustrating a use example of a test tube holder according to the present invention.

FIG. 1 is a sectional view of a test tube holder according to Embodiment 1 of the present invention. FIG. 2-A is a view illustrating a constituent component of the test tube holder according to Embodiment 1 of the present invention. FIG. 4 is a perspective view of the test tube holder according to Embodiment 1 of the present invention.

Structure of the test tube holder in FIG. 4 is described in FIGS. 1 to 3. As illustrated in FIG. 2-A, a test tube holder 9 is configured to include a housing with a spring 1 for fixing the test tube, a test tube holder main body housing 2, and a housing of a housing with a lid-like bottom part 3.

The housing with a spring 1 for fixing the test tube is described by using FIG. 2-C. An outline of a test tube for clinical use is described in "Laboratory Automation: Specimen container" issued by the National Committee for Clinical Laboratory Standards (NCCLS). When an outside diameter of the test tube is φ13, an actual size thereof is from 11.5 mm to 14.0 mm, and when it is φ16, the actual size thereof is from 15.0 mm to 17.0 mm. In a spring portion 4, a size B of an opening portion at the top thereof is 17.0 mm or below, and a size A of an open portion at the bottom thereof is 11.4 mm or more, and the spring portion 4 needs to be at least 17.5 mm long from an end face at the top. Furthermore, as illustrated in part E of FIG. 2-C, the spring portion 4 has an arc shape that is substantially equal to a circumferential line of an inner circumference.

The housing with a spring 1 is structured to have a circular shaped hollow out at the center in which a test tube is to be inserted, and the spring portion 4 inside a projection portion (arm) extending upward. Note that in this embodiment, the housing with a spring 1 is based on a cylindrical shape; however, an external shape thereof may also be a polygonal column shape as long as it is capable of perpendicularly holding the test tube by the spring portion 4 provided to the housing at an equal interval or at an equal angle. Furthermore, when the test tube is supplied to the test tube holder by a robot arm or an operator in a state where the central axis of the test tube and a central axis of the holder are misaligned, there is a possibility that the test tube or the holder may be damaged by a bottom part of the test tube coming into contact with the housing with a spring 1 of the holder. Therefore, an upper end face of the housing with a spring 1 may be processed into a shape such as a round shape or a chamfered shape so as to cause less shock even when the test tube comes into contact therewith.

Furthermore, it is preferable that the arm be provided at an equal interval so as to be a target relative to the central axis of the holder. More preferably, the interval between the arms is 4 mm or more.

When a test tube 8 is inserted or extracted, the spring portion 4 is a part that directly comes into contact with the test tube. Generally, a paper label such as a barcode label is attached to the test tube 8 for identifying a specimen housed therein. A barcode is read by using a barcode reader such as an automatic analysis apparatus for analyzing the specimen, and using data that has been read, an item and a result of an analysis are managed. When a hard metallic spring comes into contact with the barcode, however, there is a possibility that the barcode label may be scratched or stained. Therefore, it is preferable that the spring portion 4 be manufactured of resin and be integrally molded with the housing with a spring 1 for fixing the test tube.

In Embodiment 1, polyetheretherketone (PEEK) is used for the housing with a spring 1. As another industrial material, an aromatic polyether ketone material such as polyether ketone (PEK), polyether ketone ketone (PEKK), and polyether ether ketone ketone (PEEKK) is also effective.

Since the above-described materials in the Embodiment 1 are generally expensive as a resin material, it is also possible to manufacture the main body housing 2 and the lid-like bottom part 3, for example, using a different material. In Embodiment 1, polyacetal (POM) is used. By using PEEK having high strength, excellent elasticity, and excellent durability although being expensive for the housing with a spring 1 and by using an inexpensive material having excellent wear and abrasion resistance for the housing and the lid-like bottom part 3, it is possible to realize an inexpensive and highly durable test tube holder.

Furthermore, the spring portion 4 is not necessarily limited to a spring. It may be an elastic member such as rubber, for example, as long as it is capable of holding the test tube perpendicularly by contact. Furthermore, the housing with a spring 1, the main body housing part 2, the housing with a lid-like bottom part 3, and the like may be manufactured of the same material.

As illustrated in FIG. 2-B, the main body housing 2 of the test tube holder is hollow inside. A part of an outer surface of the main body housing 2 is formed to be a detachable lid. In this embodiment, a lower surface of the main body housing 2 is detachable as the housing with a lid-like bottom part 3. It is structured such that a weight 5, a sheet 13, an identification tag, and the like can be incorporated into this hollow portion in accordance with usage. In a case where a desired member is stored in the hollow portion, it is possible to hold the member within the hollow portion by engaging a hook-shaped fixing portion 7 provided to an outer circumferential portion of the housing with a lid-like bottom part 3 with a hole provided in the main body housing 2. It is preferable that the hook-shaped fixing portion 7 and the hole provided in the main body housing 2 be opened easily by a screwdriver and the like when necessary. The housing with a spring 1 and the main body housing 2 are also joined in the above-described method. Furthermore, it is also possible to use a screw type joining in which a screw portion is provided to the housing with a spring 1, the main body housing 2, and the housing with a lid-like bottom part 3.

The weight 5, which is a member that can be housed inside the main body housing part, has a proper weight. Here, necessity of the weight 5 is described. In the test tube holder according to the present invention, the main body housing is hollow inside and an outer wall is molded of resin. On the other hand, the test tube 8 generally has a diameter of 16 mm or 13 mm, and a length of 100 mm or 75 mm. The test tube houses liquid such as blood. Therefore, in a case where a specimen such as the blood is housed in the test tube having the diameter of 16 mm and the length of 100 mm, by weight of the test tube becoming heavier and a center of gravity thereof becoming higher than that of the examiner holder, the test tube holder may become unstable and may cause failure such as overturning during transfer in the transfer line.

In FIGS. 10(a) to 10(c), difference in a position of the center of gravity of the holder due to the above-described weight 5 is described. In FIG. 10(b), a position of the center of gravity of the test tube holder 9 is illustrated when 8 ml of water is poured into the test tube having the diameter of 16 mm and the length of 100 mm (as in FIG. 10(a)). In this embodiment, a diameter of the holder is 30 mm and height thereof is 42 mm, and the weight 5 is 25 g. Under the above-described condition, the center of gravity when the weight 5 is not put in the holder is illustrated in FIG. 10(c). In FIG. 10(b), a position of the center of gravity is 21.2 mm from a bottom surface of the holder, which is 40.8 mm in FIG. 10(c). Angles of inclination balance are 54.719° and 69.814°, respectively, whereby it is clear that stability of the holder is improved by the weight 5. Note that the above-described result is only an example, and does not specify weight of the weight or a shape and a size of the holder. Furthermore, it is does specify the center of gravity.

In the conventional technique, in order to prevent overturning of the holder holding a test tube, handling has been made such as to use a structure in which the test tube is stabilized by a ring-shaped groove provided to the test tube holder, which fits with a projection in a transfer rail (see, for example, Patent Literature 1). However, in this method, transfer of the test tube is performed while the ring-shaped groove of the test tube holder and the projection portion of the transfer line are always in contact with each other. Therefore, the test tube holder may be scraped after a long time of use, and a failure may be caused in which the test tube holder is no longer fitting well with the projection portion of the transfer line. In this embodiment, by housing the weight inside the test tube holder, a center of gravity of the test tube holder is lowered in a state where the test tube is installed, whereby stable transfer can be realized. Therefore, no problem is caused due to contact of the projection, an edge, and the like of the transfer line. The weight 5 may be formed of a metal.

Furthermore, a radio wave individual identification tag 6 may be incorporated in the main body housing part. The radio wave individual identification tag 6 is used, for example, in a case where a pre-recorded number (alphanumeric character or sign) unique to a tag is read, and transfer control of the test tube holder is performed based on this information. As a non-contact ID reading method using the radio wave individual identification tag 6, a technique such as the radio frequency identification (RFID) is generally used. This is a technique of writing data on a tag of about several centimeters and reading the data by a radio wave, an electromagnetic wave, and the like.

Since the RFID uses the radio wave and the electromagnetic wave for writing and reading information, however, the data may not be read well when there is an electric conductor such as a metal near the tag. This phenomenon is caused because when the electromagnetic wave is radiated on the tag for reading the data, an eddy current is generated on a metal surface of the weight, and due to an influence of the eddy current, a magnetic field is generated in an opposite direction of the electromagnetic wave that has been radiated, whereby an effect that cancels out the radiated electromagnetic wave is generated.

Figure 6:
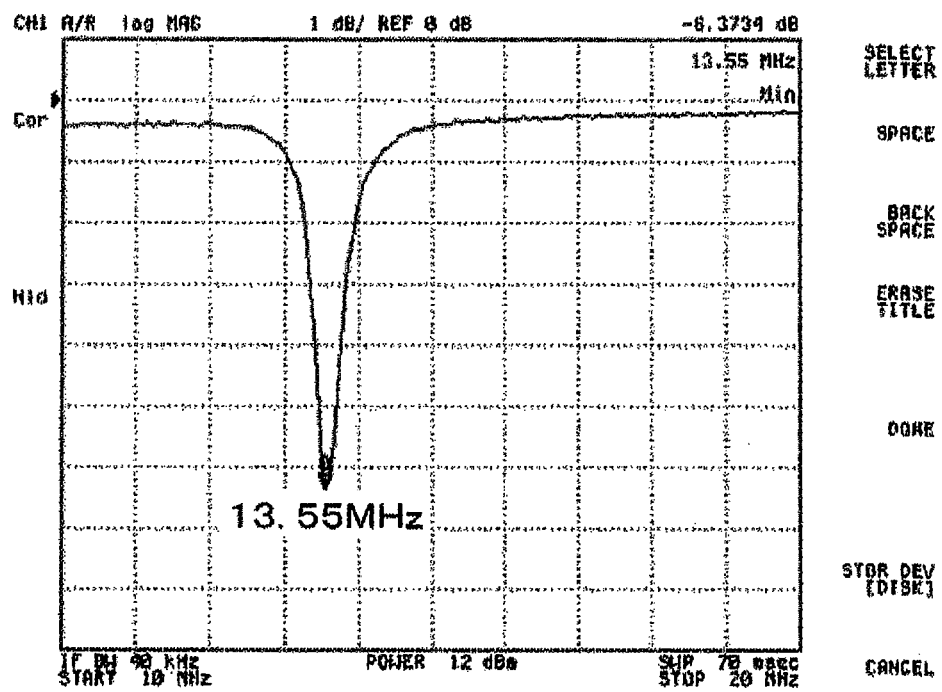
FIG. 6 is a measuring value of resonant frequency on a tag surface when a metal weight is not used.
Figure 7:
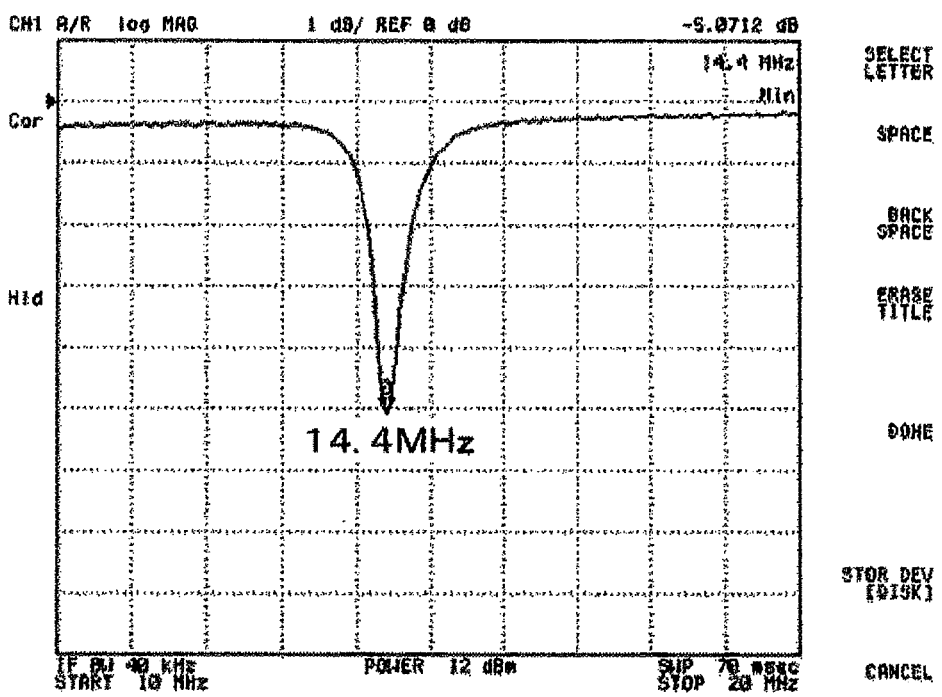
FIG. 7 is a measuring value of the resonant frequency on the tag surface when the metal weight is used.

An influence of the metal weight according to the structure of the test tube holder of the present invention is described in FIGS. 6 and 7. FIG. 6 is a resonant frequency on the tag surface when the metal weight is not used, and the frequency of the radiated electromagnetic wave is 13.55 MHz. Note that radiation of the electromagnetic wave is performed from the underside of the test tube holder. FIG. 7 is the resonant frequency measured on a surface of the individual identification tag 6 when the test tube holder has the structure illustrated in FIG. 1, the weight 5 is attached to the top of the individual identification tag 6, and the electromagnetic wave is radiated from the underside of the test tube holder under the same condition as in FIG. 6. Although the frequency of the radiated electromagnetic wave is adjusted to be 13.55 MHz, the measured frequency is 14.4 MHz, whereby it is confirmed that a phenomenon that the tag data cannot be read accurately is occurring.

Therefore, in a case where both of the metallic weight and the RFID tag are put into the hollow portion of the main body housing part, in order to prevent an RFID failure due to the metallic weight, it is preferable that an electromagnetic wave absorbent is attached between the weight 5 and the individual identification tag 6 in the hollow portion inside the test tube holder main body housing 2. As a shape of the radio wave absorbent, a sheet shape or a plate shape may be considered; however, it may also be another shape as long as it can shield an influence of the metallic weight on the RFID tag. This electromagnetic wave absorbent suppresses from becoming unable to read the tag data due to the electromagnetic wave that reaches the surface of the weight 5 and causes the eddy current on the surface thereof. Furthermore, it is also possible to suppress the eddy current by forming a grid-patterned groove on the surface of the weight.

[Embodiment 2]

Figure 8:
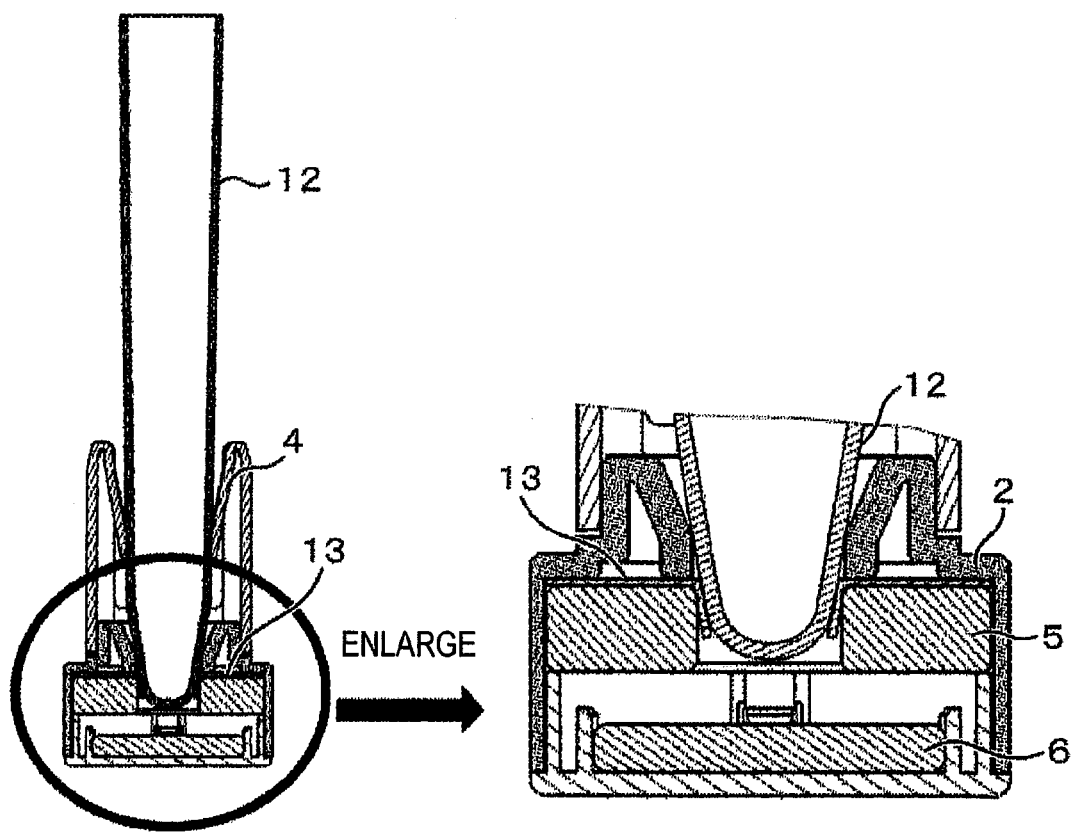
FIG. 8 is a sectional view illustrating a test tube holder according to Embodiment 2 of the present invention.

Next, Embodiment 2 is described by using FIG. 8. FIG. 8 is a view illustrating a test tube holder for holding a tapered test tube 12. It is the test tube holder incorporating a sheet 13 for holding the test tube.

Figure 9:
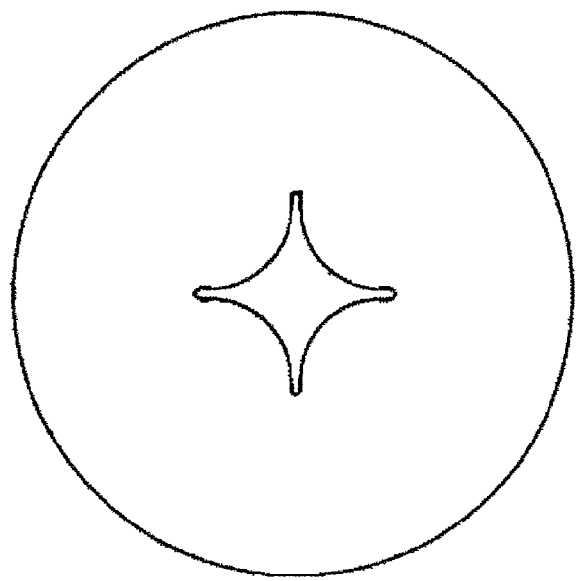
FIG. 9 is a view illustrating a sheet for fixing a lower portion of a test tube.

An example of a shape of the sheet 13 is illustrated in FIG. 9. It is a sheet having a thickness of approximately 2 mm and a cross-shaped notch at the center thereof, and silicon is a main material component thereof. In this embodiment, it is assumed that the test tube held by the test tube holder has a diameter of 16 mm or 13 mm. The test tube holder fixes an outer wall of the test tube, which has the diameter of 16 mm to 13 mm, by a spring portion 4 with holding power of 60 to 90 g. With the tapered test tube, however, the diameter thereof at a contact part with the spring portion 4 is 13 mm or below, and the spring portion may push the test tube upward along with the outer wall of the test tube. Therefore, a problem may arise in that the test tube may be floated up due to a vibration during transfer or a central axis of the test tube may be tilted.

The sheet 13 has been attached to solve this problem. It is installed in a hollow portion inside a main body housing 2 of the test tube holder, and a tip of a tapered test tube 12 is fixed by a hole of the cross-shaped notch at the center of the sheet 13. By this effect, the tip of the tapered test tube 12 can be fixed by the sheet 13, and further, it can be fixed by the spring portion 4 at the top thereof, whereby it is possible to prevent the floating up and overturning caused by the vibration of a transfer line.

Note that the shape of the sheet 13 and the shape of the hole are not limited to those in FIG. 9 as long as the tip of the tapered test tube 12 can be held. For example, it may also be a sheet provided with a hole, which is the same shape as the outside diameter of the tip of the test tube, at the center of the sheet. Furthermore, it may also be a test tube holder that supports the test tube by providing a non-sheet member capable of holding the tip of the tapered test tube inside the main body housing 2.

Note that a housing with a spring 1 for fixing the test tube and a main body housing 2 may be formed as an integral structure. The shape of the test tube is diverse, whereby it is assumed that in some cases, fixing may be incomplete by using the above-described sheet 13 and the like. In this case, in the test tube holder according to the present invention, it is possible to improve the housing with a spring 1 for fixing the test tube, and to use the test tube holder main body housing 2 and a housing with a lid-like bottom part 3 as common components, whereby it can be provided at a low cost even for a special order.

[Embodiment 3]

Figure 11:
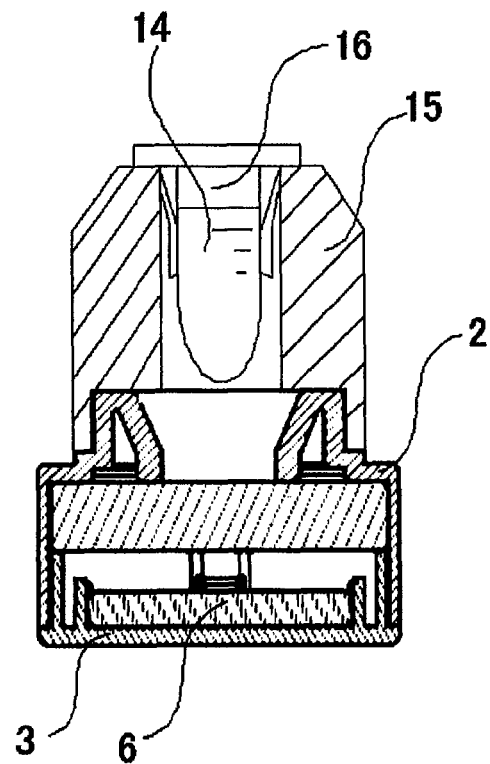
FIG. 11 is a view illustrating a test tube holder according to Embodiment 3 of the present invention.

Embodiment 3 is described by using FIG. 11.

In the fields of molecular biology and cell engineering, in order to store a small amount of specimen sample, a specimen container for holding a specimen of 2 ml or below is often used. For example, a specimen container 16 in FIG. 11 is the representative specimen container for holding the specimen of 2 ml or below. An outside diameter thereof is approximately 11 mm or below, and a length thereof is approximately 30 mm or below. It is difficult to hold this container by the housing with a spring manufactured in accordance with the above-described test tubes of φ13 and φ16.

A dedicated housing 15 has a spring portion, having the same structure as the spring portion 4 in Embodiment 1, in accordance with the outside diameter (approximately 11 mm) of the specimen container 16. To be joined with a main body housing 2, it has a fitting portion with the main body housing 2 described in Embodiment 1. Therefore, the main body housing 2 and a lid-like bottom part 3 can be manufactured using those in other embodiments, whereby even if the specimen container is a special one, it is not necessary to manufacture a specimen holder separately, and the specimen holder can be provided at a low manufacturing cost.

In Embodiment 3, the specimen container is for 2 ml or below, and the outside diameter thereof is approximately 11 mm or below, and the length thereof is approximately 30 mm or below, whereby a position of a center of gravity is lower than that of the above-described test tube of φ13 or φ16 with a length of 75 mm or 100 mm. In this case, a weight 5 incorporated into a hollow portion of the main body housing 2 is not necessary and can be removed, whereby it is possible to provide a test tube holder at an even lower cost.

[Embodiment 4]

Figure 12:
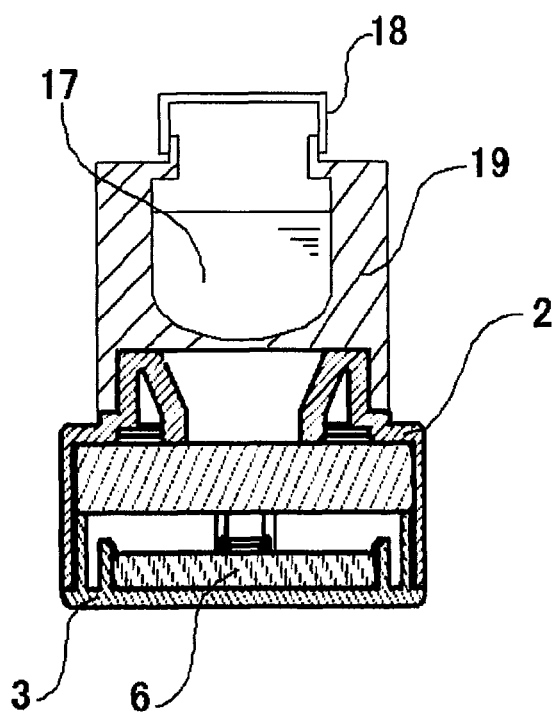
FIG. 12 is a view illustrating a test tube holder according to Embodiment 4 of the present invention.

Embodiment 4 is described by using FIG. 12.

A conventional automatic analysis apparatus that automatically analyzes a biological sample may have a configuration in which, in a case where a general sample is input into the automatic analysis apparatus in a rack, a supplying part for repeatedly supplying a standard solution rack and a control specimen rack is provided in addition to a supplying part of a general sample rack, and these two supplying parts are connected to a transfer line.

In Embodiment 4, an embodiment is described in which the above-described standard solution rack and the control specimen rack are repeatedly supplied by installing a bottle 19, which is filled with a calibration standard solution required by an automatic analysis apparatus as well as with a detergent for cleaning a flow pass of the automatic analysis apparatus, in a specimen holder.

A solution 17 is a solution different from the above-described specimen sample such as a detergent, saline, a standard solution, water, and the like. It may also be a reagent. A cap 18 prevents evaporation or leakage of the solution 17, and is screwed into a top of the bottle 19 or is attached by an inner circumference of the cap 18 adhering closely to an outer circumference at the top of the bottle 19.

In a case where the bottle 19 is mounted to the specimen holder, a housing with a spring 1 is removed from a main body housing 2, and the bottle 19 is engaged with a projection portion to which the housing with a spring 1 has been engaged. Therefore, a bottom face of the bottle 19 has a recessed structure (recessed portion) for engaging with the projection portion provided in the main body housing 2.

More preferably, in order to stably transfer a container, an outside diameter of the container is not to be exceeding the outside diameter of the main body housing part. Furthermore, in order to stably mount the container on the specimen holder, it is preferable that, when the projection portion of the housing part and the recessed portion of the bottom face of the container are engaged, a gap therebetween be 0.5 mm or below.

In this case, the specimen holder is repeatedly transferred to a dispensing position and a processing position at a specific timing from the dedicated supplying part through a transfer belt.

In a case where the specimen holder is used in this usage, the main body housing 2 and a housing with a lid-like bottom part 3 can be manufactured to have the same shape as those in the other embodiments, and even in a case where a special container other than a specimen container is placed, it is not necessary to separately manufacture the specimen holder, whereby it can be provided at a low manufacturing cost.

REFERENCE SIGNS LIST 1 housing with a spring
2 main body housing
3 housing with a lid-like bottom part
4 spring portion
5 weight
6 individual identification tag
7 hook-shaped fixing portion
8 test tube
9 test tube holder
10 transfer line
11 motor
12 tapered test tube
13 sheet
14 specimen sample
15 dedicated housing 15
16 specimen container
17 solution
18 cap
19 bottle

The invention claimed is:

1. A single specimen container holder, comprising:
   a main body housing part having a hollow portion therein and a lid member on the lower surface of the main body housing part to form a lid which is attachable to and detachable from the main body housing part;
   a holding part mounted on an upper side of the main body housing part and having an opening portion, which accepts a test tube, and a housing portion, which houses the accepted test tube; and
   an elastic part formed inside the holding part so as to abut on the housed test tube,
   wherein the single specimen container holder has a separate weight which can be stored into and removed from the hollow portion by engaging and disengaging the lid member from the main body housing part.

2. The single specimen container holder according to claim 1, wherein the holding part and the elastic part are formed of the same material.

3. The single specimen container holder according to claim 1, wherein the elastic part is a spring formed facing downward.

4. The single specimen container holder according to claim 1, further comprising a non-contact type identification tag housed inside the hollow portion.

5. The single specimen container holder according to claim 4, wherein the identification tag is an RFID tag.

6. The single specimen container holder according to claim 1, wherein
the main body housing part has a hole into which a tip of the test tube housed in the housing portion can be inserted, and
the hollow portion of the main body housing part has a support member for supporting the tip of the test tube through the hole.

7. The single specimen container holder according to claim 6, wherein the support member is a sheet using silicon as a main material and supporting the test tube by contacting a tip thereof.

8. The single specimen container holder according to claim 1, wherein
the holding part has a plurality of arms formed so as to project upward and disposed at an equal interval around the housing portion,
in each of the plurality of arms, the elastic part is formed facing the housing portion,
an upper end face of the arm is round shaped or chamfered, and
a container inside the housing portion is held by abutting the elastic part on a side wall face of the container housed in the housing portion.

9. The single specimen container holder according to claim 8, wherein the arms are installed at an interval of 4 mm or more.

10. The single specimen container holder according to claim 1, wherein
the elastic part is a spring formed downward from the opening portion side of the holding part toward the main body housing part side, and
a lower end of the spring is not in contact with the holding part.

11. The single specimen container holder according to claim 1, wherein
a bottle, which houses liquid therein and has a bottom face structure for engaging with the main body housing part, can be mounted on the main body housing part in place of the holding part.

12. The single specimen container holder according to claim 1, wherein
the opening portion can accept a test tube having a diameter of 17.0 mm or below, and
the elastic part can hold a test tube having a diameter of 11.4 mm or more, and is at least 17.5 mm long.

13. The single specimen container holder according to claim 1, wherein
the elastic part centers on a central axis of the test tube holder and has an arc shape so as to be substantially equal to a circumferential line of an inner circumference of the elastic part.

14. The single specimen container holder according to claim 1, wherein the main body housing part has a center of gravity located at a first position with respect to the lower surface of the main body housing part when the weight is not stored in the hollow portion and the center of gravity is located at a second position closer to the lower surface of the main body housing part when the weight is stored in the hollow portion.

15. The single specimen container holder according to claim 1, wherein the weight is formed of metal.

16. The single specimen container holder according to claim 15, wherein the weight has at least two grooves on a surface thereof.

17. A single specimen container holder comprising:
a main body housing part having a hollow portion therein;
a holding part mounted on an upper side of the main body housing part and having an opening portion, which accepts a test tube, and a housing portion, which houses the accepted test tube;
an elastic part formed inside the holding part so as to abut on the housed test tube; and
an RFID tag housed inside the hollow portion,
wherein the single specimen container holder has a weight housed inside the hollow portion,
the weight is formed of an electric conductor, and
the hollow portion of the main body housing part has a non-magnetic body shielding member between the weight and the RFID tag.

18. The single specimen container holder according to claim 17, wherein the weight has at least two grooves on a surface thereof.

19. The single specimen container holder according to claim 17, wherein the main body housing part includes a lid member being attachable to and detachable from a lower surface of the main body housing part.

20. The single specimen container holder according to claim 17, wherein the main body housing part has a center of gravity located at a first position with respect to the lower surface of the main body housing part when the weight is not stored in the hollow portion and the center of gravity is located at a second position closer to the lower surface of the main body housing part when the weight is stored in the hollow portion.

* * * * *